United States Patent
Gandhi

(10) Patent No.: US 9,814,403 B2
(45) Date of Patent: Nov. 14, 2017

(54) METHOD AND APPARATUS FOR MEASURING THE LEVELS OF HORMONES, NEURO TRANSMITTERS, BIO MARKERS, OR THE LIKE

(71) Applicant: Krishna Gandhi, Harrow (GB)

(72) Inventor: Krishna Gandhi, Harrow (GB)

(*) Notice: Subject to any disclaimer, the term of this patent is extended or adjusted under 35 U.S.C. 154(b) by 566 days.

(21) Appl. No.: 14/152,946

(22) Filed: Jan. 10, 2014

(65) Prior Publication Data

US 2014/0128764 A1 May 8, 2014

Related U.S. Application Data

(63) Continuation of application No. PCT/GB2012/051642, filed on Jul. 11, 2012.

(30) Foreign Application Priority Data

Jul. 11, 2011 (GB) .................................... 1111870.0
Oct. 4, 2011 (GB) .................................... 1117179.0

(51) Int. Cl.
*A61B 5/04* (2006.01)
*A61B 5/048* (2006.01)
(Continued)

(52) U.S. Cl.
CPC .......... *A61B 5/04017* (2013.01); *A61B 5/048* (2013.01); *A61B 5/0476* (2013.01); *A61B 5/14546* (2013.01); *A61B 5/7257* (2013.01)

(58) Field of Classification Search
None
See application file for complete search history.

(56) References Cited

U.S. PATENT DOCUMENTS

2003/0013981 A1* 1/2003 Gevins ................. A61B 5/0484
600/544
2007/0225674 A1* 9/2007 Molnar ............... A61N 1/36067
604/503
(Continued)

FOREIGN PATENT DOCUMENTS

CN 2782019 Y 5/2006
WO 2009055127 A1 4/2009

OTHER PUBLICATIONS

Hamid et al. "Evaluation of Human Stress Using EEG Power Spectrum"; 2010 6th International Colloquium on Signal Processing & Its Applications (CSPA).
(Continued)

*Primary Examiner* — Etsub Berhanu
(74) *Attorney, Agent, or Firm* — Eversheds Sutherland (US) LLP

(57) ABSTRACT

A method of predicting substance levels from EEG data is disclosed. The method includes analyzing EEG data to obtain the average power for each of a plurality of predetermined frequency bands and calculating a value from the average powers derived for each frequency band, said value being calculated by combining the average powers for each frequency band by dividing and/or multiplying according to a predetermined order. The method further includes obtaining an estimate of the hormone level from the equation $Y=bX+C$, where Y is the substance level to be predicted, X is the value and b and C are constants, wherein the substance is selected from hormones, neuro transmitters and bio markers.

19 Claims, 7 Drawing Sheets

(51) Int. Cl.
A61B 5/145 (2006.01)
A61B 5/0476 (2006.01)
A61B 5/00 (2006.01)

(56) References Cited

U.S. PATENT DOCUMENTS

| | | | | |
|---|---|---|---|---|
| 2008/0045853 | A1* | 2/2008 | Gluckman | A61B 5/04001 600/544 |
| 2008/0167571 | A1* | 7/2008 | Gevins | A61B 5/0484 600/544 |
| 2009/0062678 | A1* | 3/2009 | Beck-Nielsen | A61B 5/048 600/544 |
| 2009/0082691 | A1 | 3/2009 | Denison et al. | |

OTHER PUBLICATIONS

Nguyen et al. Detection of Nocturnal Hypoglycemic Episodes using EEG Signals; 32nd Annual International Conference of the IEEE EMBS, Buenos Aires, Argentina, Aug. 31,-Sep. 4, 2010.
Schutter et al. "Decoupling of midfrontal delta-beta oscillations after testosterone administration"; International Journal of Psychophysiology 53 (2004) 71-73.
Schutter et al "Salivary cortisol levels and the coupling of midfrontal delta-beta oscillations"; International Journal of Pyschophysiology 55 (2005) 127-129.
Stomrud et al. "Slowing of EEG correlates with CSF biomarkers and reduced cognitive speed in elderly with normal cognition over 4 years"; Neurobiology of Aging 31 (2010) 215-223.
Van Peer et al. "Cortisol administration enhances the coupling of midfrontal delta and beta oscillations"; Intcmational Journal of Psychophysiology 67 (2008) 144-150.

* cited by examiner

METHOD AND APPARATUS FOR MEASURING THE LEVELS OF HORMONES, NEURO TRANSMITTERS, BIO MARKERS, OR THE LIKE

CROSS-REFERENCE TO RELATED APPLICATIONS

This application is a continuation under 35 U.S.C. §120 of International Application No. PCT/GB2012/051642, filed Jul. 11, 2012 (and published by the International Bureau on Jan. 13, 2013 as International Publication Number WO 2013 008011 A1), which claims priority to (1) GB Application No. 1117179.0, filed Oct. 4, 2011; and (2) GB Application No. 1111870.0, filed Jul. 11, 2011. Each of the above-referenced patent applications is hereby incorporated by reference in its entirety.

BACKGROUND OF THE INVENTION

1. Field of the Invention

Embodiments described herein generally relate to the field of method and apparatus for measuring the levels of Hormones, Neuro Transmitters, Bio Markers or the like.

2. Description of the Related Technology

Current techniques used to measure hormone levels are extracted from blood or saliva samples. Free cortisol levels can be measured from saliva samples that are proportional to blood level cortisol. Previous studies have shown an association between EEG characteristics and cortisol indicating subjects with high cortisol levels and low cortisol levels.

Cortisol is associated with various bodily systems such as stress, exercise, hunger, sleep and released in response to fear; it is a hormone that has many knock-on effects. Typically, cortisol levels are measured from the blood or from saliva samples (which are found to be significantly associated with blood cortisol levels). The principle challenge with the current method of measuring hormones is the delay in acquiring results from blood, saliva or urine samples. The current method of obtaining cortisol measure retrospective of the time of acquisition means any error in acquisition or storage would affect the extraction of cortisol levels measured from that sample, furthermore such errors may only be detected retrospectively resulting in repeated measures and testing with additional costs. Other issues are storage and transportation of these bio samples to and from the lab. These practical issues limit the use of measuring hormones in only absolute required cases where it could otherwise be used in the decision tree for improved diagnosis or research areas.

Quantitative EEG (qEEG) techniques include the computation of power and associated scalp topographic maps for given frequency bands. Such techniques have been used during the past three decades to illustrate, diagnose and investigate neuropsychological states such as depression, alcoholism, schizophrenia or cognitive functions such as attention disorders, memory and vastly used to diagnose epilepsy.

Previous studies have investigated the relationship, either between cortisol and a neuropsychological measure of stress or between the measure of stress (such as the behavioral inhibition scale) and the EEG activity. The findings of many of these studies hover around similar accounts of these relationships which repeatedly demonstrate a correlation between the amplitudes of the delta (1-3 Hz, also categorized as slow waves) and the beta frequency bands (15-25 Hz; considered to be fast wave activity). The term 'coupling' is used when amplitudes of both the beta and delta frequencies increase or decrease together, showing coherence. The beta-delta coupling reflects increased inter-regional crosstalk in the brain which indicates high or low stress-related indices of the behavioral inhibition and anxiety scale that in turn relates cortisol levels to the coupling activity of the delta and beta frequency since cortisol is also related to stress measured by the behavioral inhibition and anxiety scale. This was further supported by Schutter and Van Honk neuroendocrinology study (Schutter, D. J. L. G., Van Honk, J., 2004. Decoupling of midfrontal delta-beta oscillations after testosterone administration. Int. J. Psychophysiol. 53, 71-73) that demonstrated beta-delta decoupling after administering testosterone, an antagonist of cortisol, i.e. low cortisol levels is associated with a lack of beta-delta coupling; termed 'decoupling'. Beta-delta decoupling is found in the subjects of the low cortisol group and beta-delta coupling in the high cortisol group. A more recent study by Van Peer et al (Van Peer, J. M., Roelofs. K., Spinhoven. P., 2008. Cortisol administration enhances the coupling of midfrontal delta and beta oscillations. Int. J. Psychophysiol. 67, 144-150) shows the direct effects of cortisol on the delta (1-4 Hz) and beta (14-33 Hz) frequency bands by administering different doses of an oral form of cortisol to participants and compared changes in their EEG pre and post cortisol administration. The finding revealed that increased dosage of cortisol resulted in beta-delta coupling at the mid-frontal region (FZ) further supporting the relationship between beta-delta activity of the EEG spectrum and cortisol. These studies demonstrate a close relationship with EEG activity and hormones, indicating the potential to use the EEG data to predict measures of hormones levels.

SUMMARY

Embodiments of the present invention attempt to at least partially address the problem of providing a non-invasive measurement technique for measuring the levels of hormones in the body.

In a first aspect, the present invention provides a method of predicting substance levels from EEG data, comprising the steps of:

analysing EEG data to obtain the average power for each of a plurality of predetermined frequency bands;

calculating a value from the average powers derived for each frequency band, said value being calculated by combining the average powers for each frequency band by dividing and/or multiplying according to a predetermined order; and obtaining an estimate of the hormone level from the equation:

$$Y = bX + C$$

where Y is the substance level to be predicted, X is the value and b and C are constants, wherein the substance is selected from hormones, neuro transmitters and bio markers.

The EEG data may be acquired from any number of channels and locations from which the associated frequency bands are derived from and used in the calculation to predict hormone levels, neurotransmitter or biomarker. In an embodiment, the EEG data is collected from at least two electrode positions. The average power spectrum may be obtained by a Fast Fourier Transform of artefact free EEG data or recording of the acquired EEG data.

In one embodiment, the method is applied to EEG data which has been pre-recorded. In a further embodiment, the method further comprises measuring the EEG data. The Data may be measured for at least 30 s.

In some embodiments, the value is a ratio obtained by combining the average powers for each frequency band by dividing and/or multiplying according to a predetermined order.

In an embodiment, the frequency bands are selected from delta, theta, alpha, beta, smr, high beta and gamma. Typically, these bands are taking to encompass the frequency ranges: The exact boundaries vary but the general frequency bands are: delta 1-3 Hz; theta 3-7 hz; alpha 7-11 hz; beta 11-25 hz; smr 15-19 hz; highbeta 20-30 hz and gamma 35 hz+.

In an embodiment, the predetermined frequency bands are the frequency bands which have a correlation with increasing or decreasing levels of the substance to be measured in any measurable medium such as blood, urine or saliva.

These frequency bands may be obtained by retrieving this information from a database or the like as this information should be the same for a particular substance. In a further embodiment, the method further comprises determining the predetermined frequency bands by:

measuring the average power for a plurality of frequency bands for a plurality of substance levels and selecting the bands which show a correlation with increasing or decreasing substance levels.

How the average powers are combined to calculate the value or ratio will also be fairly constant for the same substance and hence this information can be saved and retrieved when required. In a further embodiment, the method further comprises determining how the ratio should be calculated by:

measuring the average power for the predetermined frequency bands for a plurality of substance levels;

calculating a plurality of ratios or values, wherein each ratio or value is calculated by varying how the average power of the frequency bands are combined; and plotting the plurality of calculated ratios or values for each substance level against substance level and selecting the ratio which provides a plot closest to a straight line.

In a further embodiment, the boundaries of the predetermined frequency bands are varied to see if a better correlation to a straight line can be achieved.

The ratio is an expression of the relationship of the powers of the associated frequency bands as a single quantitative value that is found to correlate with the hormone, neurotransmitter or biomarker.

Similarly, the constants b and C are likely to be the same for the same substance and hence do not need to be derived for each measurement of the same substance. However, in a further embodiment, the method comprises determining the constant b and C by:

measuring the average power for the predetermined frequency bands for a plurality of substance levels;

plotting the ratio for each substance level against substance level, fitting a straight line to the plot and deriving b and C.

In a further aspect, the present invention provides an apparatus for predicting substance levels from EEG data, the apparatus comprising a processor configured to:

receive EEG data;

analyze said EEG data to obtain the average power for each of a plurality of predetermined frequency bands;

calculate a value from the average powers derived for each frequency band, said value being calculated by combining the average powers for each frequency band by dividing and/or multiplying according to a predetermined order; and obtain an estimate of the hormone level from the equation:

$$Y = bX + C$$

where Y is the substance level to be predicted, X is the ratio and b and C are constants, wherein the substance is selected from hormones, neuro transmitters and bio markers.

In a further embodiment, the substance is cortisol. Here, the predetermined frequency bands are the Theta, Alpha, Delta and SMR bands. In one embodiment, they are divided in the order of Theta/Alpha/Delta/SMR such that the ratio is obtained by multiplying the average power of the theta and smr frequencies and dividing it by the multiplication of the average band power of the delta and alpha frequencies.

However, the method can be used for many different substances including hormones such as cortisol, testosterone etc. and neuro-transmitters, bio markers etc.

Methods in accordance with embodiments of the present invention provides a method of measuring hormone levels from EEG data. In an embodiment, recording of EEG data should preferably last at least two minutes. This data is processed to obtain the average powers for the delta, theta, alpha and smr bands used in a calculation to generate a single value or an amalgamated ratio. This amalgamated ratio is entered into a regression line formula to predict the salivary cortisol levels that are most accurate at approximately twenty minutes from start of recording.

The acquired EEG measures from electrode placement at FZ on the scalp are processed to obtain the average powers for the delta band, theta band, alpha band & smr band with a suitable computerized algorithm, in this case the Truscan EEG-NFB system has an inbuilt Fast Fourier Transformation (FFT) software to obtain the average power for each frequency band required to calculate salivary cortisol levels. A FFT is processed on artefact free portions of EEG data this is generally all activity over 50 Hz to eliminate electrical noise or noise from other sources. A ratio of the average power for each associated frequency band is calculated to provide a single amalgamated value. To predict salivary cortisol levels from this value it is entered in a regression formula found at the research stage when plotting the ratio against the actual measures of cortisol. This predicted measure is accurate where r is between 0.068 and 0.073 for a window of approximately 40 minutes after the EEG baseline acquisition.

A method in accordance with an embodiment of the present invention comprises the following steps:

The baseline EEG data is recorded over a minimum period of at least two minutes, preferably where the subject has refrained from any consumption of food, drink, drugs or engagement of any form of exercise.

A FFT is performed on noise free portions of EEG data from each electrode channel against a reference electrode calculating the frequency band power at a series of frequency points over a frequency range/band.

An average scalp power spectrum is computed by calculating the mean power (at each frequency point) at the scalp electrode(s)

A ratio of the average power of each associated frequency band is calculated to provide a single amalgamated value and entered as 'x' in the regression line equation to find the predicted salivary cortisol level.

Reduction in the amalgamated power ratio of the delta (1-4 hz), theta (4-7 hz), alpha (7-12 hz) & smr (12-19 hz) frequency bands indicate low levels of salivary cortisol, respectively, a high amalgamated power ratio indicate high levels of salivary cortisol. Substituting the calculated amalgamated power ratio into a derived regression line formula provides predicted levels of salivary cortisol where r=0.73, p=0.01.

The primary advantage of measuring cortisol from acquired EEG data is that it provides almost real time measures. Secondly the method of using EEG data to measure hormone levels in the body avoids extracting any biosamples or invasive procedures. These features allow instant measures of hormones and measures of multiple hormones from the same EEG recording as well as repeated measures instantly which solves the time lag issue of current methods of measuring hormone levels in the biological system. Instant results, repeated measures and of more than one hormone is achieved with this method that derives the measures from acquired EEG data. The benefits of having instant measures of any hormone facilitate improved diagnosis through the clinician being further informed. Additionally hormone measures can be acquired from subjects that do not necessarily indicate a requirement of hormone testing. Information of hormone levels in the body are important as they make up the regulatory system that is related with most disorders reflecting some abnormality in the hormones levels eventually if not initially. The device can be included in a normal check up routine that can capture subtle illness/disorders in the early stages leading to more of an accurate diagnosis.

In embodiments of the present invention the methods described above are implemented as a smart phone application. In embodiments, the EEG data may be measured using an EEG headset connected to smart phone or computer via a wireless connection such as Bluetooth. In such an arrangement, application or software processes the data received and does not require a wired connection to the EEG capture device. Embodiments of the present invention have the advantage that movement restrictions due to wired connections to the EEG capture device are removed. Further such a system would require less time to set up and be lightweight and simple to use.

Such an application may send the results to a server over the internet and be operable to produce reports over time or other variables.

Embodiments are envisaged in which EEG data is sent to a server for remote processing and analysis. Such embodiments allow remote processing.

BRIEF DESCRIPTION OF THE DRAWINGS

The present invention will now be described with reference to the following non-limiting embodiments in which.

DETAILED DESCRIPTION OF CERTAIN INVENTIVE EMBODIMENTS

Figure 1:
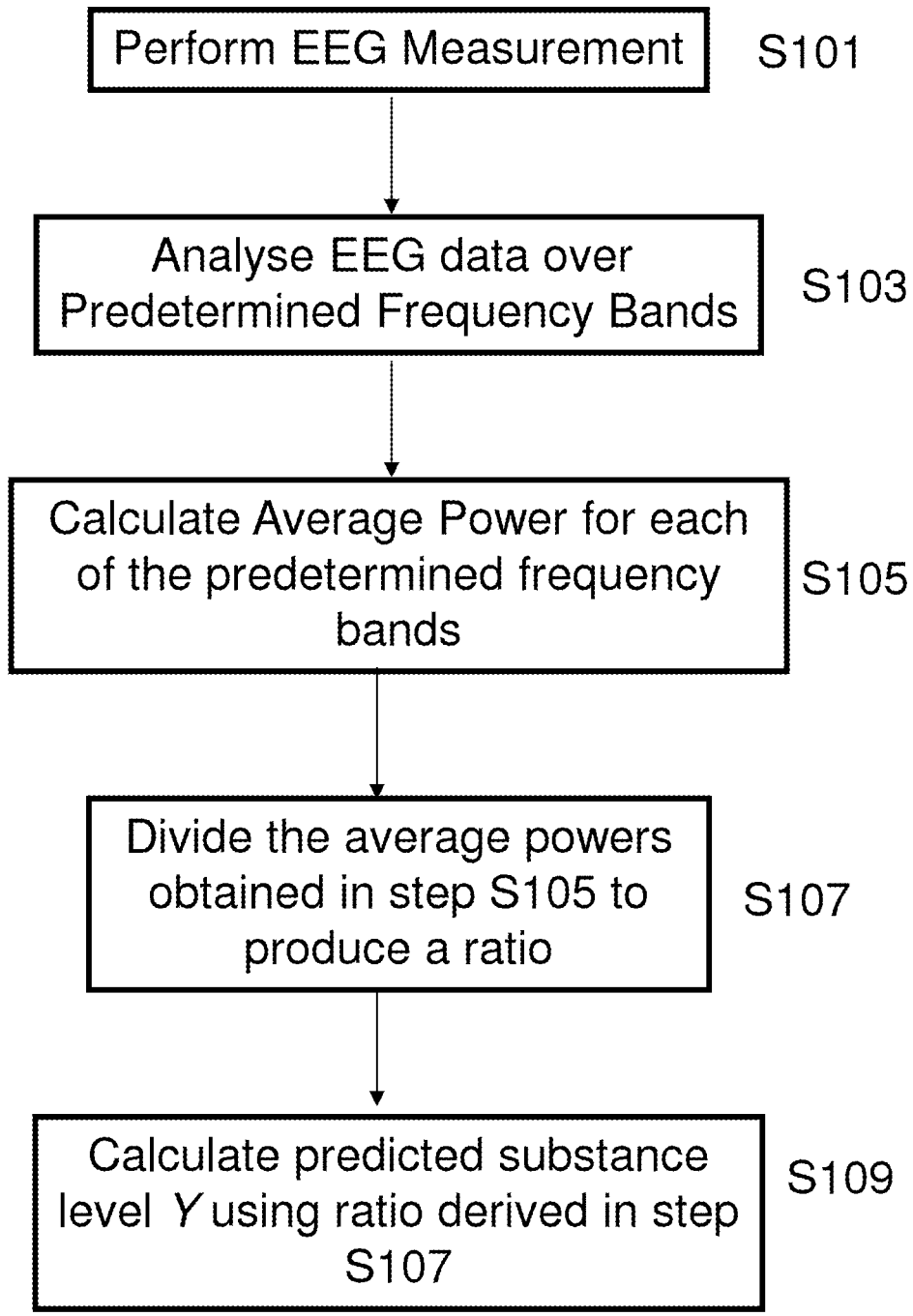
FIG. 1 is a flow diagram showing a method in accordance with an embodiment of the present invention.

FIG. 1 is a schematic of a flow diagram showing a method in accordance with an embodiment of the present invention. In step S101, an EEG measurement of a subject is performed. In step S103, the EEG data is analyzed over predetermined frequency bands. This analysis may be performed as the EEG is measured or the analysis may be performed off-line.

Figure 2:
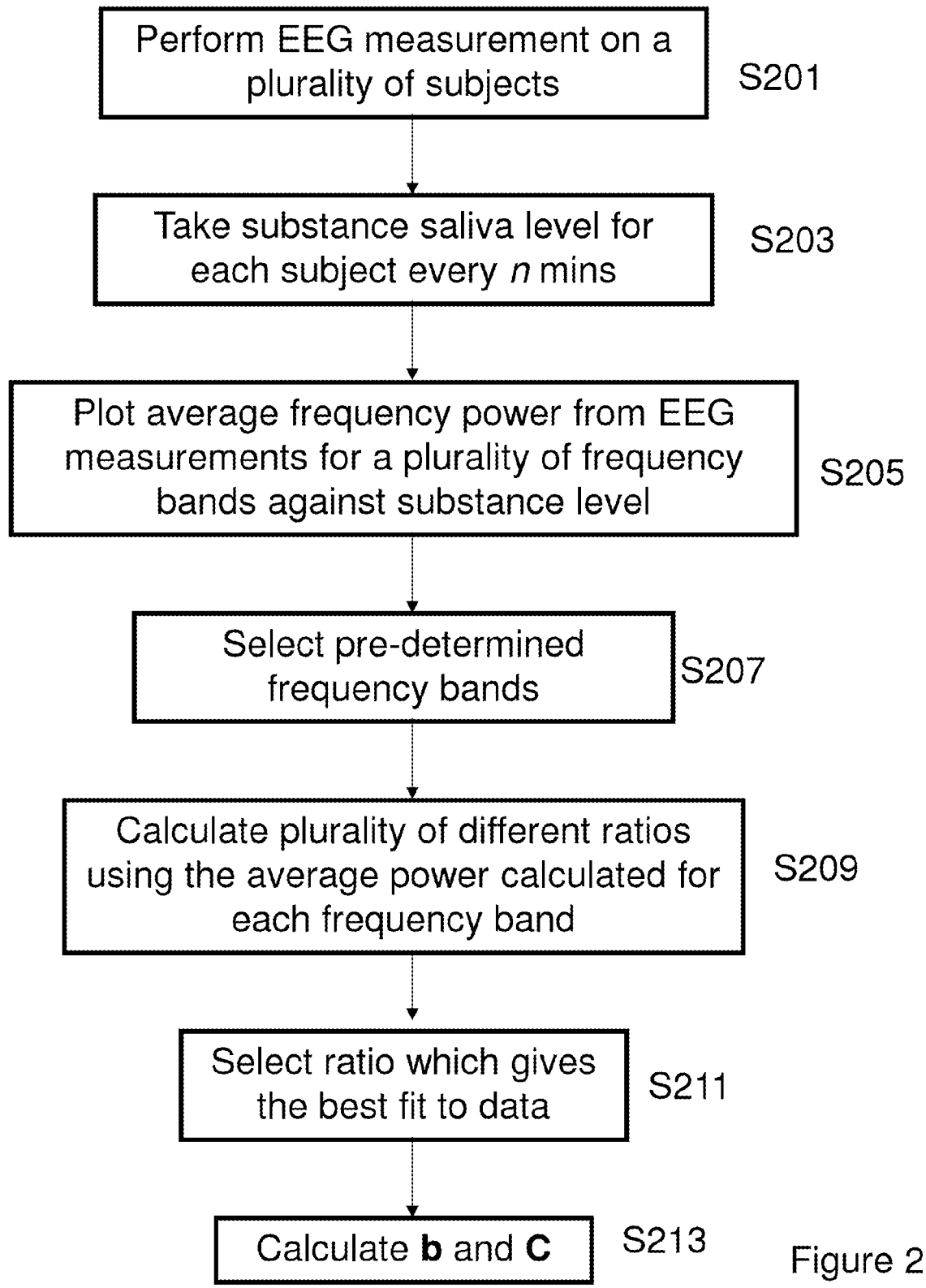
FIG. 2 is a flow diagram showing a method for determining the parameters used in the method described with reference to FIG. 1.

There are a number of frequency bands which can be analyzed. Typically, the predetermined frequency bands will be selected from the known bands of delta, theta, alpha, beta, SMR, high beta and gamma. Which frequency bands are chosen will depend on the substance which is to be measured. FIG. 2 will explain methods for selecting the frequency bands for a particular substance. Once the frequency bands have been determined for a particular substance, they can be used for all analysis of a particular substance.

In one embodiment, the frequency bands will be selected in step S103 from the well-established frequency bands. However, as will be described with reference to FIG. 2, some variation in these bands is also possible.

Next, the average power for each predetermined frequency band is calculated in step S105. Calculation of the average power for a frequency band is a well-known technique and can be performed using known FFT techniques.

Next, a single ratio will be determined from the average powers calculated in step S105. The ratio will be determined by dividing the average powers. However, the ratio will be different dependent on the order in which the average powers are divided. The order in which the average powers will be divided is predetermined and will be explained with reference to FIG. 2. Once the order has been determined, this can be saved and looked up when performing method step S107.

Finally, in step S109, the substance level is calculated using the ratio derived in step S107 and by using the equation:

$$Y=bX+C$$

where b and C are constants which can be looked up for a particular substance. How these constants are derived will be described with reference to FIG. 2. X is the ratio derived in step S107 and Y is the substance level to be determined.

In FIG. 1, a method has been described where the predetermined frequency bands, the order in which the average powers should be combined and also the constants used to predict the substance level have been determined. Once these variables have been determined, they can be saved and accessed when the equipment is next required to perform the analysis for a specific substance.

FIG. 2 outlines the method for determining these variables. Typically, the method will require measurements be performed on a plurality of subjects. In one particular embodiment, at least 100 subjects are used.

EEG measurements are performed on the plurality of subjects in step S201.

In this particular example, the substance level to be determined will be measured using an invasive technique for each subject every n minutes in step S203. For example, if the substance level, for example cortisol, is to be measured from saliva, a saliva sample can be taken every 5 mins. It is also possible to measure the substance level from other fluids in the body such as blood, urine etc.

Each subject will have a different substance level. Therefore, by taking measurements from the plurality of subjects, it is possible to obtain the average frequency power for each band for a range of different substance levels. This is plotted in step S205. It will be seen at this point that some frequency bands will change with the varying substance level. For example, with increasing substance level, the average power will also increase or decrease in substance level, the average power will increase. The frequency bands where there is a change in the average power with substance level will then be selected in step S207. The frequency bands which show a dependence in their behavior on the substance level will vary dependent on the substance.

These the frequency bands which will then be used as the predetermined frequency bands in step S103 of the method of FIG. 1. In step S203, it is explained that the substance level is taken every n minutes. When the average frequencies are plotted in step S205, a different plot is created for each time when the substance level is taken. The substance level will vary over time. For example, it is believed that the substance level measured in the saliva 20 min after an EEG reading will correspond to the substance level measured during the EEG reading. This is because there is a delay in the time which the effects measured in the brain take to filter through to the saliva.

The average powers calculated in step S205 for the predetermined frequency bands are divided. The order in which the power levels are divided and multiplied is important as the order will affect the results.

For example, if there are three power levels A, B, C—these can be combined:

$$\frac{A}{B*C},$$
$$\frac{A*C}{B},$$
etc.

The average power levels are combined in different ways by dividing and multiplying to provide a plurality of different ratios or single values in step S209. For example, in one embodiment, it is possible to combine the above 3 values:

$$\frac{1}{A*B*C},$$

These are then plotted against the measured substance levels and the ratio which gives the best fit to a straight line is selected.

Once this ratio has been selected, b and C are calculated in step S213.

It is possible to also improve the correlation to a straight line by slightly varying the boundaries on the predetermined frequency bands. Therefore, the process may be repeated by varying the boundaries on the frequency bands in step S205 to see if a better correlation can be obtained.

To demonstrate that QEEG measures can be used to predict hormones, neurotransmitter levels in any bodily sample in particular predicting salivary cortisol levels a study was conducted on 27 normal healthy participants aged between 20-50 years in the psychology cubicle at the University of Westminster, Regent Street campus almost every weekday over a six week period. Criteria also included participants to be clear of any psychiatric conditions, significant medical disease and past head injury with loss of consciousness greater than 5 minutes. Due to variations in cortisol levels over the day, testing began between 2-2.30 pm and lasted between 60-75 minutes, allowing the study to be conducted on one subject per day. This constraint limited the amount of time to test 27 subjects which were recruited via personal contacts and others who were interested in the study. All subjects were sent an information sheet and a consent form before their scheduled date of participation. Contents on the information sheet, stating consumption of food and any form of stimulants including exercise should be avoided an hour before the experiment was verbally reiterated to the subject, the evening prior to their participation in the experiment.

Three salivary samples were collected for each subject, one immediately before (Cor A) and two after the EEG baseline. The second (Cor B) and the third (Cor C) samples were taken 20 and 40 minutes respectively after the EEG baseline to see how they relate in terms of time based on a time lag in the cortisol response. Saliva samples were collected using salivettes and stored in the freezer.

Both the ear lobes and area FZ were cleaned with alcohol wipes, followed by the Nuprep gel, Electrode were attached using the 10-20 conductive gel and recording began once the impedance fell below 5 K$\Omega$. Most subject details and settings were entered and configured prior to the subjects' arrival. Protocol configuration included setting the beta frequency band between 15-26 Hz and the delta frequency band between 1-4 Hz. The EEG was recorded at low cut off set at 0.5 Hz, high cut off at 50 Hz and the notch filter at 60 Hz to minimize artefact contamination.

Following the skin preparation, electrodes were attached to each lobe and a single electrode attached at region FZ. To get accurate EEG baseline measures each participant underwent a practice EEG baseline recording before the true EEG baseline recording of 3 minutes. Three salivary cortisol samples per subject were taken using salivettes during the session. The first cortisol sample (CorA) was collected immediately before the EEG baseline recording which serves as the baseline cortisol measure, a second sample (CorB) was taken 20 mins after the EEG baseline and the third cortisol sample (CorC) was taken 40 minutes after the EEG baseline. The salivette consists of a cotton swab in a labelled tube and was placed on the tongue directly from the cap of the tube so to avoid any contact, once moist enough the subject was asked to roll the swab under their tongue for 3 minutes. The subject placed the swab directly into the tube and capped securely.

For the EEG baseline recording, subjects were asked to maintain a fixed gaze on a spot before them in order to minimize ocular movements and to avoid any muscular movement which would otherwise produce artefact in the baseline recording.

On completion of data collection each salivette was placed in its labelled tube and packaged in an ice box for cortisol assaying. The samples were measured twice however due to lack of saliva content in samples of four subjects' cortisol levels could not be acquired, resulting in a sample size of 23 subjects.

The Truscan 32 qEEG-NFB system was used to measure the EEG activity at FZ based on the findings of Van Peer et al. The EEG measures and amplifies signal from the electrodes positioned on the surface of the scalp. This data is normally presented as wave activity from each electrode/channel. A FFT inbuilt in the system's software is applied to the EEG data from each channel to provide average power values for each frequency band where in general, activity between the range of 1-4 Hz is delta; 4-8 Hz is theta; 7-12 Hz is alpha; 12-15 Hz is smr; 15-20 is beta; 20-25 Hz is high beta and 25 Hz+ is gamma.

The associated frequencies used in the amalgamated ratio for cortisol were derived from plotting the average power for each frequency band for each subject against the corresponding cortisol level. Frequencies that showed a clear relationship with cortisol levels determined which frequency powers were used in the amalgamated ratio which captured the relationship of each frequency band with respect to each other in a single quantitative value as a correlate of cortisol.

Results showed a strong relationship between the ratio of theta, alpha, smr, delta power i.e. the amalgamated ratio of these frequencies from location FZ at time 1 and salivary cortisol levels. The same was seen between time 1 and subsequent salivary cortisol levels at Cor B taken at time 2 and Cor C at time 3. Table 1 shows EEG data and cortisol samples measures for each subject, with Pearson's correlation in percentage for each sample against the EEG ratios. As shown in Table 1 the strongest EEG correlation showed to be with salivary cortisol levels Cor B measured at time 2.

TABLE 1

| Subject | Thealphdel | TheAlpDelSmr | CorA | CorB | CorC |
|---|---|---|---|---|---|
| 204 | 0.0307 | 0.00576 | 2.3583 | 1.1895 | 1.44569 |
| 205 | 0.02143 | 0.00345 | 3.1496 | 2.8107 | 2.08844 |
| 207 | 0.04105 | 0.0057 | 3.1745 | 2.9693 | 2.5346 |
| 208 | 0.06615 | 0.0117 | 4.8166 | 4.613 | 3.5523 |
| 209 | 0.04482 | 0.00799 | 3.1058 | 2.4622 | 2.01053 |
| 210 | 0.051 | 0.01015 | 3.4505 | 2.8355 | 2.35246 |
| 212 | 0.04595 | 0.00981 | 2.8896 | 3.1472 | 2.95327 |
| 213 | 0.04741 | 0.00765 | 5.0527 | 3.6563 | 2.65358 |
| 214 | 0.02394 | 0.00312 | 2.4702 | 1.8513 | 1.89469 |
| 216 | 0.0796 | 0.02254 | 9.9285 | 6.6087 | 4.02475 |
| 217 | 0.03887 | 0.00657 | 5.8141 | 4.249 | 3.38738 |
| 218 | 0.08308 | 0.01887 | 9.9955 | 7.2797 | 5.90102 |
| 219 | 0.06608 | 0.01121 | 4.3041 | 3.3824 | 1.96916 |
| 221 | 0.04371 | 0.00573 | 4.0396 | 2.6629 | 2.20028 |
| 222 | 0.021 | 0.00457 | 5.7281 | 2.8212 | 2.34813 |
| 223 | 0.06545 | 0.0162 | 2.3552 | 2.1495 | 2.3593 |
| 224 | 0.04389 | 0.00522 | 2.7916 | 2.0631 | 1.23415 |
| 225 | 0.03484 | 0.00727 | 3.0324 | 1.6176 | 1.29367 |
| 226 | 0.03535 | 0.00613 | 2.8807 | 2.7616 | 2.86363 |
| 227 | 0.05505 | 0.01203 | 4.3902 | 4.1014 | 3.51314 |
| 228 | 0.06662 | 0.01037 | 5.1246 | 3.68 | 2.53074 |
| 229 | 0.04325 | 0.00657 | 1.4735 | 1.0408 | 1.414 |
| 230 | 0.04964 | 0.00761 | 4.0565 | 3.8902 | 2.53005 |
| | thealphdel | | 60.73% | 70.84% | 62.81% |
| | TheAlpDelSmr | | 68.33% | 72.72%* | 68.38% |

*The strongest correlation of 73% at p = 0.01 between the EEG ratio: TheAlpDelSMR and Cor B.

Figure 3:
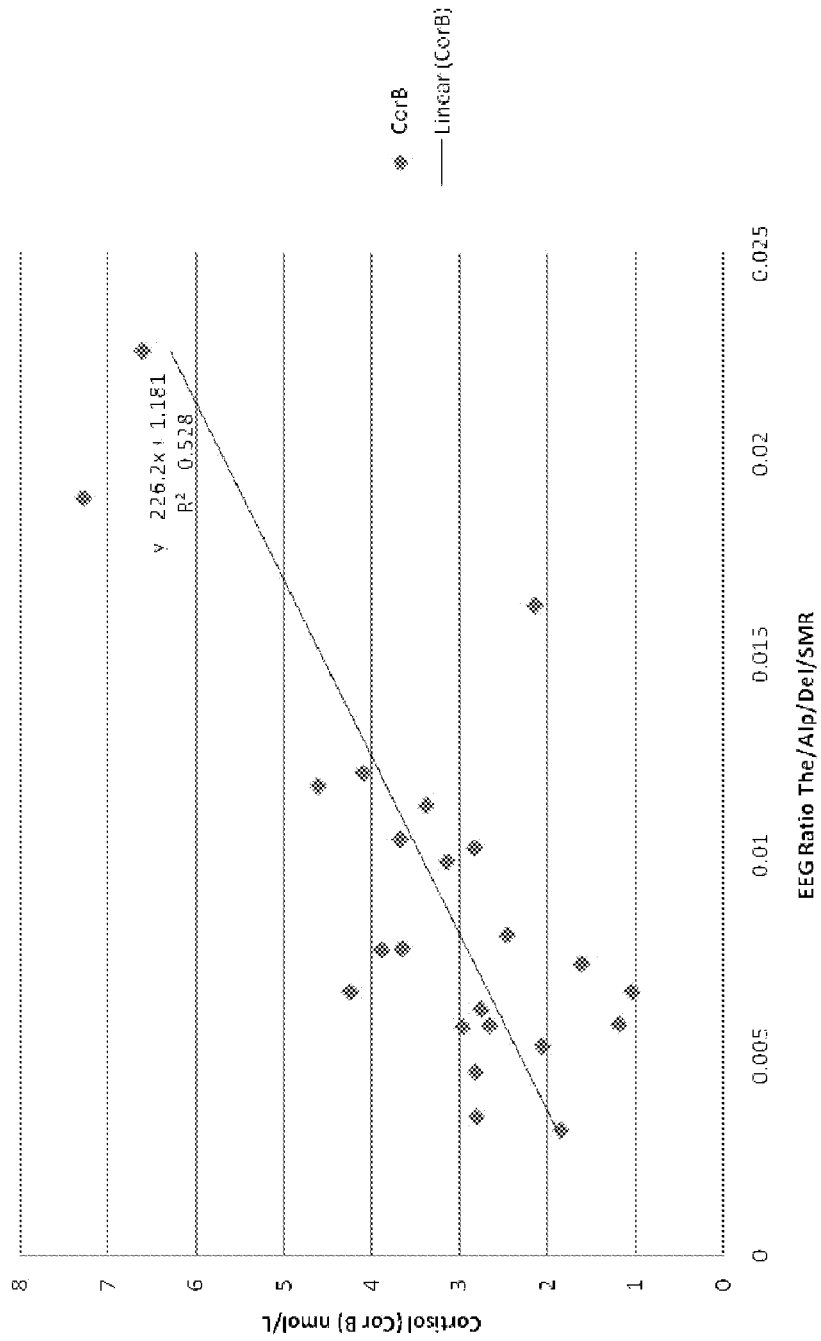
FIG. 3 is a plot of the cortisol level taken from salivary samples plotted against the calculated amalgamated power ratio for each subject.

Across the 23 subjects' data illustrated in FIG. 3, Pearson's correlation coefficient is highly significant at r=0.73, p=0.01 between the EEG ratio and Cor B.

Thus the relationship between the alpha, theta, delta and smr power levels allow the levels of salivary cortisol to be predicted from a window of 40 mins from recording the EEG with the most accurate level of prediction at 20 minutes after EEG recording. The lag time could be a result of the time taken for the series of events from the Hypothalamus-Pituitary-Adrenal axis to the corresponding cortisol levels being reflected in the saliva.

In particular, the power relationship of these frequencies as a ratio provides a quantitative measure of salivary cortisol. For research use or as an applied form of therapy, the effects or efficacy of the therapy can be evaluated by reference to the predicted cortisol levels.

The method of calculating cortisol levels from a sample of artefact free EEG recording can be computerized or automated using appropriate software built into an EEG data acquisition device or in an external device that can analyze data from the EEG.

A predictive approach may use regression, a statistical procedure that regularly follows that of a correlation. A "line of best fit" or "regression line" is plotted to the data, using least square criterion (This can be computerized easily via any number of computerized statistical packages). Cortisol levels are predicted by entering the amalgamated ratio of the frequencies as X in the regression line equation:

$$\text{Where } Y = bX + c$$

Predictive example based upon the 23 subjects' data illustrated in FIG. 3 Pearson's correlation coefficient, r=0.7275 with a slope of regression line, b=227.51 and the constant at 1.1899. Each subject's values are based on 3 minutes of artefact free high quality data acquired from location FZ.

FFT provided the average power, a quantitative value for each frequency band that is divided by each other respectively and entered as X in the above regression equation to find salivary cortisol value, Y.

Figure 4:
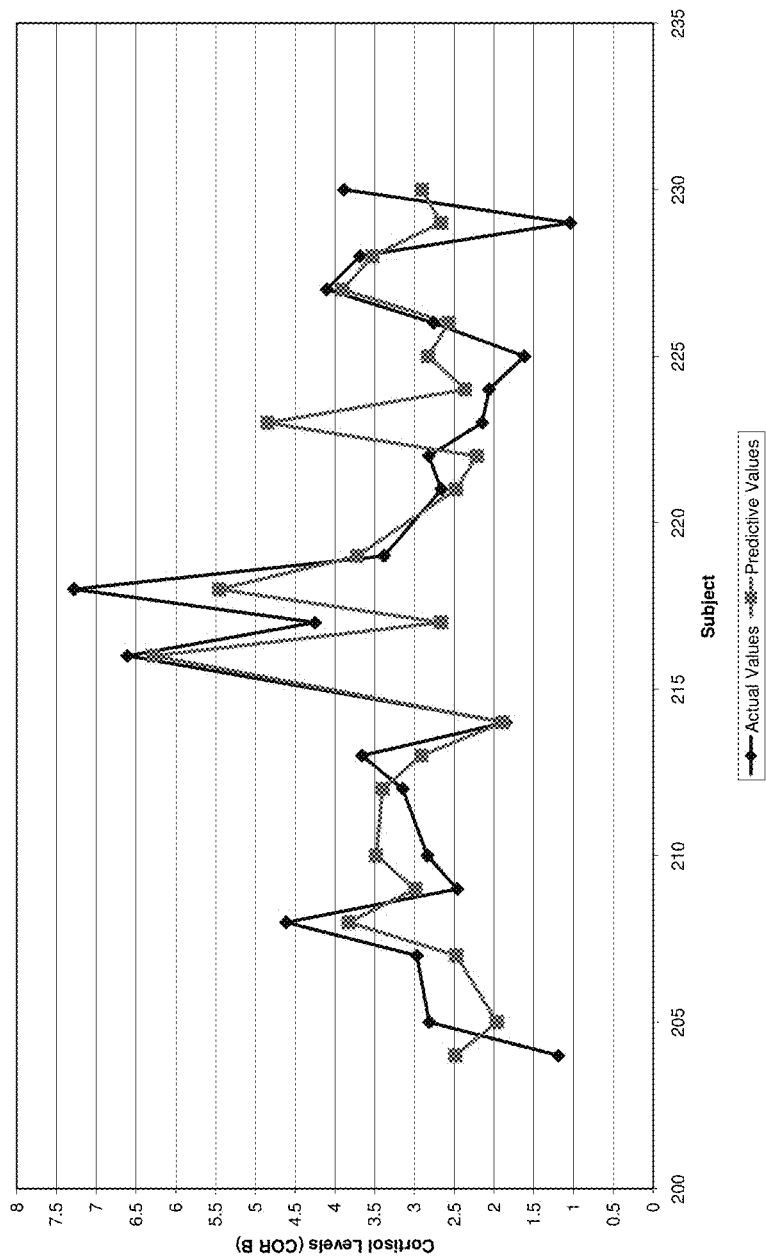
FIG. 4 is a plot of the actual measures of cortisol levels for each subject against the predicted measures for each subject.

FIG. 4 shows a graph of actual measures of Cor B and predicted Cor B (found by entering the EEG calculated ratio into the regression line formula) for each subject on the x-axis.

It can be seen here that the predictive cortisol levels are very close to the actual values. The general trend of both lines are similar. Subject 221 actual and predictive cor b values are almost identical. Subject 205, 223 are outliers, where the predictive value is away from the actual value.

Figure 5:
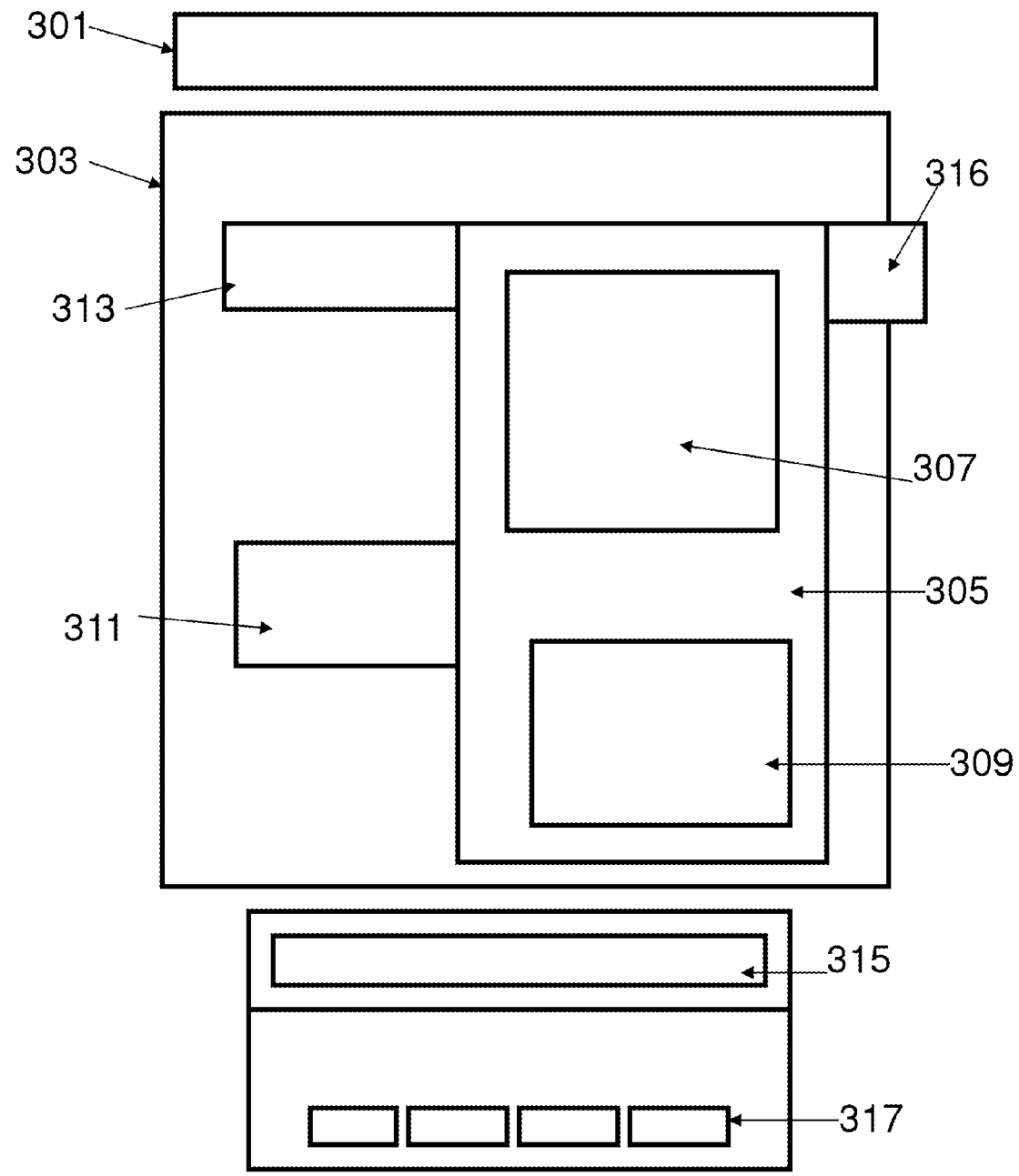
FIG. 5 is a schematic of the hardware used in apparatus in accordance with an embodiment present invention.

A schematic of the hardware which may be used in accordance with an embodiment of the present invention is shown in FIG. 5. Electrodes are attached to a subject in order to perform the EEG analysis. The electrodes 301 are connected to central unit 303. Central unit 303 comprises a central processing unit 305.

This particular embodiment, the central processing unit 305 has two functions, the first is performed in section 307 where signal processing is performed on the signal received from the electrodes. This will involve methods such as amplification, filtering the signal and performing FFT analysis resulting in separated preconfigured bands and their respective mean powers. In section 309, the analysis as described with reference to steps S107 to S109 (from FIG. 1) is performed. An algorithm is used to predict the selected hormone or neurotransmitter on the processed EEG data resulting in a numeric value of that hormone or neurotransmitter. As explained with reference to FIG. 1, in order to perform a method of FIG. 1, certain parameters need to be established for each substance. If the parameters have been established for the substance 311.

The central unit is powered by power supply 313. It contains USB 316 in order to provide a hardwired connection to devices such as external memory etc.

The results are then displayed on display 319. The system is controlled by control panel 317.

In one embodiment, the central unit 303 is configured to receive downloads relating to the parameters required for a particular substance. Therefore, the same EEG system may be used for many different measurements.

In this particular system, the electrodes 301 are connected directly to the EEG system which analyses the data. However, it is possible for the data to be analyzed off-line.

Figure 6:
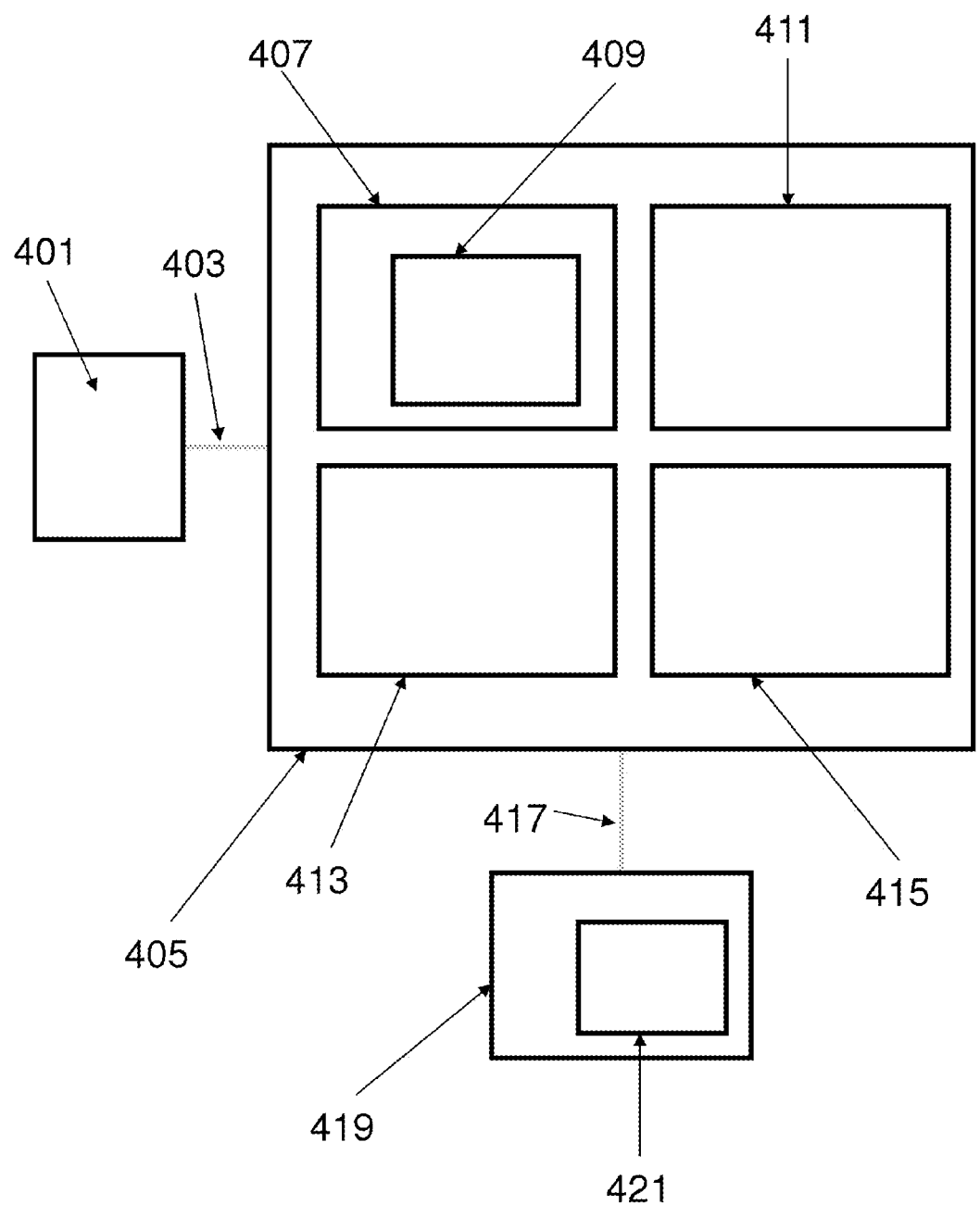
FIG. 6 is a schematic of the hardware used in accordance with an embodiment of the present invention which is implemented as a smart phone application.

FIG. 6 shows a schematic of an embodiment of the present invention implemented as a smart phone application. An EEG capture device 401 is connected via a wireless connection 403 to a smart phone 405. In this embodiment, the EEG capture device 401 is a Bluetooth EEG headset and the wireless connection 403 is a Bluetooth connection. The smart phone 405 has a processor 407 which executes the smart phone application 409. The smart phone application 409 implements a method as described in reference to FIG. 1. The smart phone has a memory 411 which stores data used by the application 409. The smart phone has a user interface 413 through which a user can control the smart phone 405 and input data. In this embodiment the user interface 413 is a touch screen interface. The smart phone 405 has a display 415 which displays information to a user. The smart phone 405 has an internet connection 417 through which the application 409 can connect to a server 419. The server 419 stores data 421 which can be accessed by the application 409. The data 421 stored on the server 419 may include pre-calculated variables determined using the method shown in FIG. 2. The server 419 may store data and algorithms for measuring predicting the levels of substances from EEG measurements. In addition, the smart phone may upload data calculated from by the application to the server 419 for storage and may access historical data from the server 419 for comparison with newly calculated data.

Figure 7:
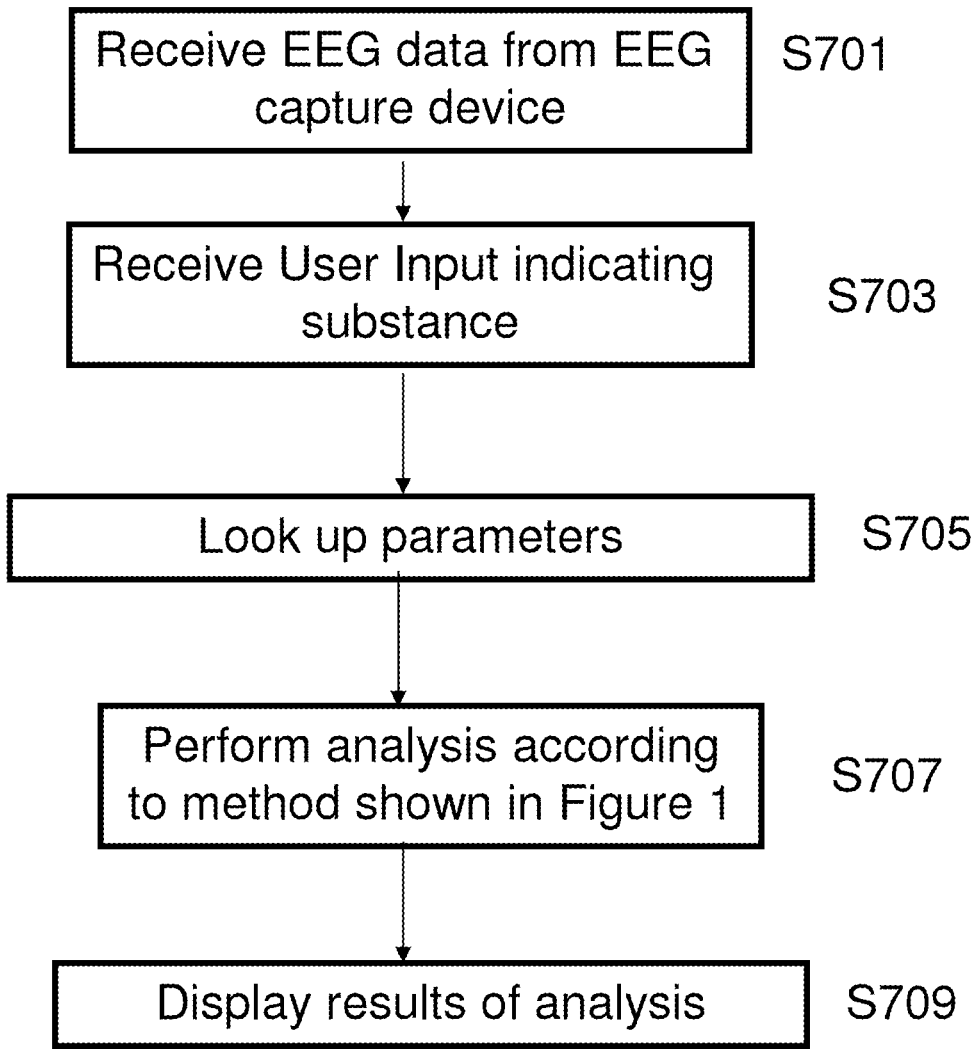
FIG. 7 is a flow diagram showing a method in accordance with an embodiment of the present invention which is implemented as a smart phone application.

FIG. 7 shows a flowchart of the steps carried out by a smart phone application in accordance with the present invention. In step S701, the smart phone 405 receives EEG data from the EEG capture device 401. In step S703, the smart phone 405 receives a user input indicating the substance which is to be measured from the EEG. The application 409 causes the display 415 to display a series of buttons. The buttons allow the user to choose the biomarker, neurotransmitter, or hormone to measure. The application 409 may also allow the user to configure the variables and determine how the EEG data is processed.

In step S705, the application 409 looks up the parameters required for processing the EEG data required to carry out the calculations inputted by the user in step S703. In this embodiment, the application 409 looks up the parameters from the memory 411. IN other embodiments, the application 409 may look up the parameters from the server 419 over the internet.

In step S707 the application carries out analysis using the method described in reference to FIG. 1. In step S709, the results of the analysis are displayed to the user.

In embodiments the results of the analysis are stored in the memory 411 of the smart phone 405. The smart phone may upload the results of the analysis to the server 419 and download previous results for comparison with the newly calculated results.

In the above embodiment, the processing takes place on the smart phone 405, however, embodiments of the present invention are anticipated in which the EEG data is sent to a remote server and the calculations are carried out on the remote server.

The foregoing only describes one example of the invention, and modifications which are obvious to those skilled in the art may be made thereto without departing from the scope of the invention as defined in the accompanying claims. For example, the general methodology of this invention may be applied to measuring or predicting the levels of other hormones such as testosterone, progesterone, oestrogen, cortisol and neurotransmitters in the blood or saliva, where the method is the same with three different factors: The location of acquiring EEG activity, it could be from a single or multiple locations of the scalp, the regression equation based on a amalgamated ratio derived from the power of the associated frequencies that is correlated with the substance of measure.

Further, while in the example given above an embodiment is describe in relation to a smart phone connected by Bluetooth to an EEG headset, those of skill in the art will understand that embodiments of the present invention may be implemented on other devices, for example a desktop or laptop computer, a tablet computer or other device. In the embodiment describe above, the user interface is a touch screen interface, those of skill in the art will realise that any method of user input may be used, for example, the user interface may be a keyboard or keypad, a mouse, trackball or trackpad or other input device. While the embodiment described above includes an EEG headset, any other EEG capture device may be used and this may be connected to the device carrying out the calculation by a wired connection such as a universal serial bus (USB) connection, a wireless connection such as a Wi-Fi connection or any combination of the two.

What is claimed is:

1. A computer implemented method of determining a substance level in a body of a human or non-human animal subject, the method comprising:
   obtaining EEG data comprising EEG signals collected from the subject and analyzing the EEG data to obtain the average power for each of a plurality of frequency bands;
   calculating a value from the average powers derived for each frequency band, said value being calculated by combining the average powers for each frequency band by dividing and/or multiplying according to a predetermined order, wherein the predetermined order is determined based upon the substance; and
   obtaining an estimate of the substance level from the equation $Y=bX+C$,
   where Y is the substance level to be predicted, X is the value and b and C are constants,
   wherein the substance is selected from hormones, neuro transmitters and bio markers.

2. The method of claim 1, wherein the value is a ratio of selected ones of the average powers.

3. The method of claim 1, wherein the frequency bands are selected from Delta, Theta, Alpha, Beta, SMR, High Beta and Gamma.

4. The method of claim 1, wherein the substance is cortisol.

5. The method of claim 4, wherein the frequency bands are the Theta, Alpha, Delta and SMR bands.

6. The method of claim 5, wherein the bands are divided in the order of Theta/Alpha/Delta/SMR.

7. The method of claim 1, wherein the EEG data is collected from the human or non-human animal subject for at least 30 seconds.

8. The method of claim 1, wherein the EEG data is collected from at least two electrode positions.

9. The method of claim 1, wherein the frequency bands are the frequency bands which have a correlation with increasing or decreasing levels of the substance.

10. The method of claim 1, further comprising selecting the frequency bands by measuring the average power for a plurality of frequency bands for a plurality of substance levels and selecting the bands which show a correlation with increasing or decreasing substance levels.

11. The method of claim 1, further comprising:
determining, for each of at least three levels of the substance, a corresponding set of average power values to provide a plurality of sets of average power values, wherein each set of average power values comprises an average power value for each of the frequency bands;
selecting a method of combining the average power values of the sets to provide a test value for each set, each test value corresponding to a level of the at least three levels of the substance;
wherein the selecting comprises varying how the average power of the frequency bands are combined and selecting the method of combining which provides a relationship between the test values and the corresponding at least three levels of the substance that is closest to a straight line.

12. The method of claim 11, further comprising varying the boundaries of the frequency bands to obtain a better correlation to a straight line.

13. The method of claim 1, further comprising determining the constant b and C by:
measuring the average power for each of the frequency bands for each of at least three substance levels to obtain a corresponding at least three values;
fitting a straight line to the at least three substance levels and the corresponding at least three values; and
deriving the constants b and C based on the fitting, wherein the fitting a straight line comprises fitting the substance levels as a function of the values.

14. The method of claim 1, wherein obtaining the EEG data comprises receiving the EEG data over a wireless link.

15. The method of claim 1, further comprising receiving an input from a user, the input indicating at least one substance, the level of which is to be predicted.

16. The method of claim 1, further comprising looking up values for the constants b and C.

17. A tangible non-transitory carrier medium comprising computer readable instructions configured to cause a computer executing said instructions to perform the method of claim 1.

18. A computer apparatus for predicting substance levels in a body of a human or non-human animal subject, the computer apparatus comprising a processor configured to:
receive EEG data comprising EEG signals collected from the subject;
analyse said EEG data to obtain the average power for each of a plurality of predetermined frequency bands;
calculate a value from the average powers derived for each frequency band, said value being calculated by combining the average powers for each frequency band by dividing and/or multiplying according to a predetermined order, wherein the predetermined order is determined based upon the substance; and
obtain an estimate of the substance level from the equation $Y=bX+C$,
where Y is the substance level to be predicted, X is the value and b and C are constants, wherein the substance is selected from hormones, neuro transmitters and bio markers.

19. A computer implemented method comprising:
obtaining EEG data based on EEG signals collected from a human or non-human animal subject having a body;
analyzing the EEG data to obtain an average power value for each of a plurality of frequency bands of the EEG data to provide a plurality of average power values;
calculating a value from the average powers derived for each frequency band, wherein the value is calculated by scaling at least a first one of the plurality of average power values using at least a second one of the average power values; and
determining an estimate of a level of a substance in the body of the human or non-human animal subject from which the EEG signals were collected;
wherein the substance is selected from hormones, neuro transmitters and bio markers, and
wherein the estimate is determined based on the value and stored data describing a regression line relationship between the value and the level of the substance.

* * * * *